US006810755B1

(12) United States Patent
Pask et al.

(10) Patent No.: US 6,810,755 B1
(45) Date of Patent: Nov. 2, 2004

(54) PERMEAMETER SYSTEM AND METHOD TO DETERMINE SOIL HYDRAULIC CAPACITY FOR ONSITE WASTEWATER SYSTEMS

(75) Inventors: David A. Pask, Morgantown, WV (US); Michael L. Aiton, Point Marion, PA (US)

(73) Assignee: West Virginia University, Morgantown, WV (US)

( * ) Notice: Subject to any disclaimer, the term of this patent is extended or adjusted under 35 U.S.C. 154(b) by 112 days.

(21) Appl. No.: 10/317,829

(22) Filed: Dec. 11, 2002

Related U.S. Application Data

(60) Provisional application No. 60/339,915, filed on Dec. 11, 2001.

(51) Int. Cl.[7] ............................. G01N 1/00; G01N 1/04; G01N 15/08; E21B 47/10
(52) U.S. Cl. ........................ 73/863; 73/864.43; 73/38; 73/152.41
(58) Field of Search ......................... 73/864.44–864.45, 73/864.41, 152.41, 3, 312, 864.43; 324/600; 175/50; 702/12

(56) References Cited

U.S. PATENT DOCUMENTS 5,803,664 A * 9/1998 Kawabata et al. ....... 405/128.5
6,098,448 A * 8/2000 Lowry et al. .................. 73/38
2002/0095984 A1 * 7/2002 Johnson .................. 73/152.05

* cited by examiner

Primary Examiner—Hezron Williams
Assistant Examiner—Tamiko Bellamy
(74) Attorney, Agent, or Firm—Steptoe & Johnson PLLC

(57) ABSTRACT

A permeameter having a hollow tube with a second tube slidably disposed within an internal chamber of the hollow tube, used in combination with one or more tables each of which correlates a specific rate of reading fall rate of water within the hollow tube with a unique soil hydraulic capacity of the soil being tested. The second tube has an air hole and a slot which are used in causing water contained in the hollow tube to seep into an auger hole. A reducing connector is secured to the bottom of the hollow tube which provides the means for maintaining the second tube within the internal chamber of the hollow tube. The second tube is secured in the extended position by a compression fitting attached to the reducing connector. A conventional measuring tape, having consecutive markings showing continuous ¼, ½, and 1 inch distances, is affixed to the outside surface of the hollow tube such that the numbers extend vertically along the length, or longitudinal central axis, of the hollow tube. The permeameter is used in combination with one or more charts which maps a range of reading fall rates with a corresponding soil hydraulic capacity. The charts are created by a series of formulas using known soil absorption principals, the dimensions of the permeameter, the dimensions of an auger hole in the soil, and the level of a water line in the auger hole.

25 Claims, 9 Drawing Sheets

|   | A | B | C | D | E | F | G | H | I | J |
|---|---|---|---|---|---|---|---|---|---|---|
| 1 |   |   |   |   |   |   |   |   |   |   |
| 2 |   |   |   |   |   |   |   |   |   |   |
| 3 | Pask Permeameter - Calibration | | | | | | | | | |
| 4 |   |   |   |   |   |   |   |   |   |   |
| 5 | Reservoir diameter Inches |   |   | 3 |   |   |   |   |   | 0.030654683 |
| 6 | Depth of water in hole (inches) |   |   | 8 | 0.6667 |   |   |   |   | 0.006076389 |
| 7 | Diameter of auger hole (inches) |   |   | 3 |   |   |   |   |   | 5.044881683 |
| 8 | Time to fall one inch * |   |   |   | 8 Minutes | | 45 Seconds | | Q gal/ | 5.333333333 |
| 9 |   |   |   |   |   |   |   |   | h/r | 5.238744549 |
| 10 |   |   |   |   |   |   |   |   | sqrth/ | 2.792528803 |
|   |   |   |   |   |   |   |   |   | 2pi h^ | |
| 11 | Permeability U.S. Gallons / Square feet/day | | | | | = | 2.453706387 | = | 1.16E-06 m/sec | |
| 12 |   |   |   |   |   |   |   |   |   |   |
| 13 | Standard soil absorption rate (SAR) | | | | | 0.8 gal/sq.ft./day | | | | |
| 14 | Application rate (gal/sq.ft./day) | | | | | 0.817902538 | | | | |
| 15 | Design Flow (gal/day) * | | | 240 | | | | | | |
| 16 | Area of SAS (sq.ft.) | | | | (theoretical) | 293.4334946 | | | | |
| 17 |   |   |   |   |   |   |   |   |   |   |
| 18 |   |   |   |   |   |   |   |   |   |   |
| 19 | Minimum area of Soil Absorption System (SAS) | | | | | | 300 Square feet | | | |
| 20 |   |   |   |   |   |   |   |   |   |   |
| 21 | Data entry point * | | | | | | | | | |

FIG. 9

NOTE  Corresponding formulae are given on the following sheet.

| | A | B | C | D | E | F | G | H | I | J |
|---|---|---|---|---|---|---|---|---|---|---|
| 1 | | | | | | | | | | |
| 2 | | | | | | | | | | |
| 3 | Packer Permeameter - Calibration | | | | | | | | | |
| 4 | | | | | | | | | | |
| 5 | Reservoir diameter inches | | | 3 | | | | | | =((D5)^2*PI()*7.4938/(4*1728)) |
| 6 | Depth of water in hole (inches) | | | 8 | =D6/12 | | | | | =(D8*60+F8)/86400 |
| 7 | Diameter of auger hole (inches) | | | 3 | | | | | | =J5/J6 |
| 8 | Time to fall one inch | | | 8 | Minutes | 45 | Seconds | | Q gal/day hr | =D6/(D7/2) |
| 9 | | | | | | | | | sqrt(h)^2-1 | =SQRT(J8^2-1) |
| 10 | | | | | | | | | 2pi h^2 | =2*PI()*E8^2 |
| 11 | Permeability U.S. Gallons / Square feet/ day | = | | | | =J7*(LN(J8+J9)-1)/J10 | = | =F11/(24.543*86400) | m/sec | |
| 12 | | | | | | | | | | |
| 13 | Standard soil absorption rate (SAR) | | | | 0.8 | gal/sq.ft./day | | | | |
| 14 | Application rate (gal/sq.ft./day) | | | | | =F11/0.5^0.666667 | | | | |
| 15 | Design Flow (gal/day) | | | 240 | | | | | | |
| 16 | Area of SAS (sq. ft.) | | (theoretical) | | | =D15/F14 | | | | |
| 17 | | | | | | | | | | |
| 18 | | | | | | | | | | |
| 19 | Minimum area of Soil Absorption System (SAS) | | | | | =IF(F:4>E13,D15/E13,F16) | Square feet | | | |
| 20 | | | | | | | | | | |
| 21 | Data entry point * | | | | | | | | | |

FIG. 10

PERMEAMETER SYSTEM AND METHOD TO DETERMINE SOIL HYDRAULIC CAPACITY FOR ONSITE WASTEWATER SYSTEMS

RELATED APPLICATION

This application claims the benefit of U.S. patent application 60/339,915, filed Dec. 11, 2001.

BACKGROUND OF THE INVENTION

1. Field of the Invention

This invention relates generally to the design of wastewater and stormwater systems using soil infiltration, and more particularly, to a simplified apparatus and method for determining the maximum soil hydraulic conductivity of soils found above the water table.

2. Related Art

Soil is used to accept wastewater every day from well over 25 million homes in the United States. In addition, soil's infiltration capacity is used everyday in trenches for storm water runoff and for centralized irrigation systems. Currently, standard percolation tests and/or soils analysis by direct observation and field soil texture determinations is used to determine how to design trenches and other soil based treatment methods for handling wastewater and to estimate the hydraulic capacity of the soil. Significant levels of error occur in such conventional percolation testing procedures including human error, measurement error, and variability in the test procedure due to the falling head pressure as the water drops in a percolation test hole. Soils analysis in the field is a subjective test procedure relying solely on the skill of the individual practitioner in properly characterizing the soil and then "inferring" the soil hydraulic capacity from the soils analysis. These older methods fail to take into account such problems as compaction of the soil, and also require highly skilled practitioners to get a reasonably reliable guess of the soil's ability to accept wastewater for treatment. These sources of testing error result in high failure rates for wastewater methods using soil based treatment and disposal and significant errors in estimating maximum hydraulic capacity of unsaturated soils near the ground surface.

Permeameters have been designed and used to determine soil infiltration capacity, however, the art has not developed simplified design methods for in-the-field applications. One conventional permeameter apparatus that defines the prior art is a permeameter apparatus that was originally devised by Mr. David Pask about 20 years ago. The fundamental principle of this device is based upon Marriottes Apparatus first devised in the $18^{th}$ Century and results in a constant head water column in the soil hole being tested. However, adoption of this device and earlier methods has not occurred because of difficulty of use of the earlier methods. In addition, similar devices require careful setup and adjustable versions were prone to jamming and leakage. As an example, the Guelph Permeameter used by soil scientists has multiple joints that must be air and watertight and uses a separate air tube to determine the water level in the hole augered in the ground. The Guelph permeameter also has the disadvantage of requiring a perfectly vertical setup.

Other earlier methods include a nomogram developed by David Pask that had flaws in its application which prevented its adoption in the United States. An application of this Pask developed nomogram method includes the application of this different design methodology with an earlier public domain version of the present permeameter. In addition, Amoozegar's Permeameter described in 1989, has a complicated series of tubes to provide the constant level (head) of water in the hole. Thus, the Amoozegar permeameter uses a more complicated Mariottes apparatus that is not well suited to field applications and has no connection to design methodology. Other examples of apparatus and methods for determining soil hydraulic capacity using constant head methods include Stewart, U.S. Pat. No. 5,322,629, and Ankeny et al, U.S. Pat. No. 4,884,436. These apparatuses are comparable only in the sense that they use constant head arrangements or sometimes require the use of excessive quantities of water for testing (Stewart) but once again provide no methodology. Numerous other patents on methods using permeameters to estimate hydraulic conductivity can be found. However, these methods usually require collection of soil samples and processing in the laboratory, injection of gas into the soil, use of semipermeable membranes to estimate conductivity based on pressure differentials, etc. These other methods result in either: potential errors from disturbing or modifying conditions in the native soil, or the targeting of hydraulic conductivity below the water table or in the bedrock, and both are outside the scope of this invention.

In addition to the above, conventional approaches to onsite system design for treating wastewater and storm water are driven by "prescriptive" regulations. That is, the designers of such onsite systems merely apply state regulations and guidelines in their designs. The disadvantages with such an approach is that the specific attributes and characteristics of the target property and the type of soil are not taken into account, often resulting in failure of the system to handle the amount of wastewater.

Therefore, there is a need for a simplistic permeameter apparatus with an accompanying design methodology based on soil performance that can be used easily in the field and is accurate as to estimating the tested soils permeability and maximum hydraulic capability.

SUMMARY OF THE INVENTION

The present invention solves the problems encountered with conventional permeameter apparatuses and methods with an improved, simplified permeameter for use in soil infiltration applications such as onsite wastewater and storm water treatment systems. The permeameter of the present invention is a hollow tube having a second tube slidably disposed within an internal chamber of the hollow tube. The second tube also has an air hole and a slot which are used in causing water contained in the hollow tube to seep into an auger hole. A reducing connector is secured to the bottom of the hollow tube which provides the means for maintaining the second tube within the internal chamber of the hollow tube. The second tube is secured in the extended position by a compression fitting attached to the reducing connector. A conventional measuring tape, having consecutive markings showing continuous ¼, ½, and 1 inch distances, is affixed to the outside surface of the hollow tube such that the numbers extend vertically along the length, or longitudinal central axis, of the hollow tube.

The permeater of the present invention also uses multiple tables, each of which correlates a specific reading of rate of fall rate with a unique soil hydraulic capacity. The tables are calculated according to conventional soil absorption principals while taking into account the dimensions of the permeameter, the dimensions of the auger hole, and the level of the water line in the auger hole. When used in the field, a user simply determines a stabilized rate of falling water within the hollow tube and uses this stabilized rate to "look up" in the table a corresponding soil hydraulic capacity of the tested soil. This methodology allows the user to base his/her analysis and design of onsite systems for treating wastewater and storm water on the performance of the soil, and not merely on prescriptive regulations.

The apparatus and method of this invention provides an efficient and accurate means for determining soil permeability (also called hydraulic conductivity). Results of testing with the method and apparatus of this invention are used to make a number of site design decisions, including bottom area of trench required, amount of water each trench can accept given the site constraints, how far apart the trenches should be once the loading for each trench is known, and whether a soil absorption system is acceptable at that site.

The apparatus of this invention is an improved version of Marriottes Apparatus in which a small diameter hole in the wall of the tube replaces the internal vent tube. This small diameter hole controls the entry of air into the reservoir to release the flow of water according to the demand. In addition, the apparatus includes a chart for instantly converting the fall in reservoir height for saturated soil conditions (measured in minutes per inch) to trench design loading rate ("DLR Trench"). The apparatus may optionally include additional charts converting the raw fall in reservoir height data into other useful information such as, but not limited to, maximum design loading rate for the soil ("MDLR Soil"), trench hydraulic capacity ("THC"), or trench separation.

In operation, the permeameter of this invention is used to determine, among other things, the trench design loading rate ("DLR"). Once the proper location(s) for testing soil permeability has been established, the permeameter is filled with water, inverted, and inserted into a hole augered into the soil. In a preferred embodiment, a 3 inch diameter hole is bored into the upper horizon of the soil to a depth of 18 to 20 inches using a hand auger. After a period of several minutes, preferably about 5 minutes to about 10 minutes, a stop watch is used to time the fall of the water level in the reservoir. Once the minutes/inch rate of fall is consistent for each reading time period, a steady state of saturated soil conditions around the auger hole has been established. This rate of fall data is then used to determine the previously mentioned site characteristics, i.e., DLR Trench, MDLR Soil, THC, and trench separation.

An advantage of the invention is that saturated conditions are reached quickly around a test hole because of the test holes' small size.

Another advantage of the invention is that whether saturation conditions have been reached can be easily determined by monitoring the drop of the water level in the permeameter. As a result, soil percolation testing using the permeameter of the present invention can be done much more rapidly than standard percolation testing.

Another advantage of the invention is that the results of the testing with the permeameter of the present invention can be used to make a number of site design decisions, such as, but not limited to bottom area of trench required, how much water each trench can accept given the site constraints, how far apart the trenches should be once the loading for each trench is known, and whether a soil absorption system is acceptable for the site.

Another advantage of the invention is that various useful results can be obtained simply by looking to a supplemental chart instead of requiring sophisticated data interpretation.

Another advantage of the invention is that it is ideal for field use, and it can be easily used and interpreted by a novice operator.

Another advantage of the invention is that the permeameter can be used either in a vertical or tilted arrangement in an auger hole.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 9 is a spreadsheet showing the calculation of an entry in the second column of Table 1 and Table 2 for the preferred embodiment of the present invention with a reading fall rate of 8.75 minutes/inch; and FIG. 10 is a spreadsheet showing the formulas for calculating the entries of the second column of Table 1 and Table 2.

DETAILED DESCRIPTION OF THE PREFERRED EMBODIMENTS

A. Permeameter Apparatus

Figure 1:
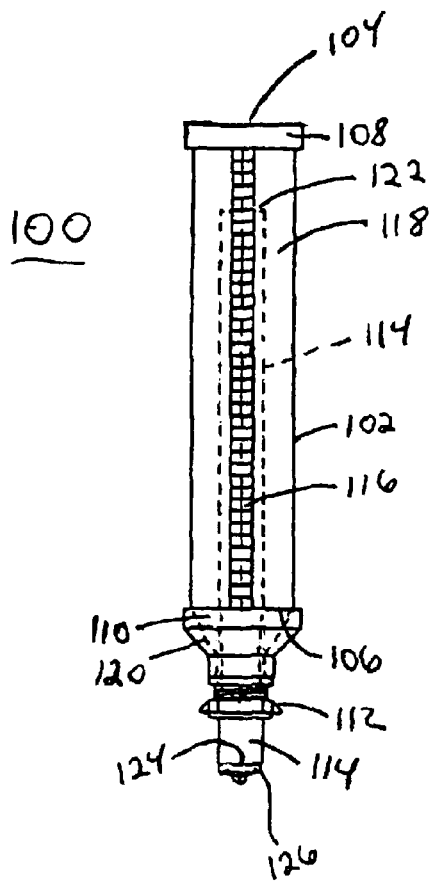
FIG. 1 is a planar front view showing a permeameter of the present invention.

The permeameter 100 of the present invention is shown in FIG. 1. The permeameter 100 is a hollow tube 102 having a top end 104, a bottom end 106, a diameter (width of the hollow tube 102), and an internal chamber 118. The top end 104 of the hollow tube 102 is sealed both air and watertight by a cap 108 which is removably secured to the top end 104. A second tube 114, having a top end 122, a bottom end 124, a diameter (width) smaller than the diameter of the hollow tube 102, is slidably disposed within the internal chamber 1118 of the hollow tube 102.

Figure 2:
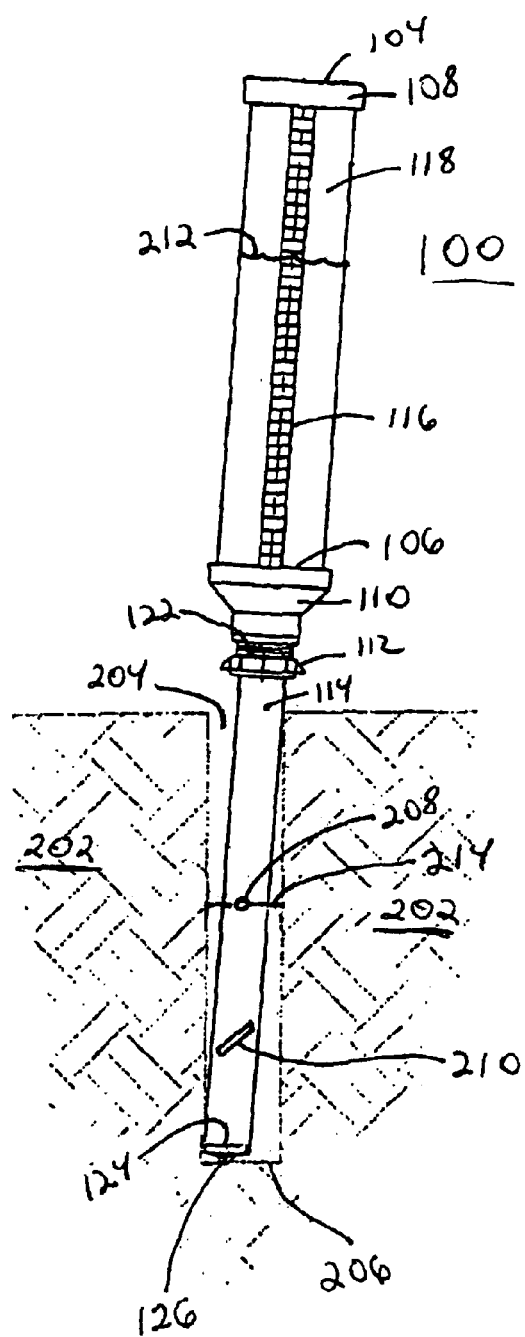
FIG. 2 is a planar front view of a permeameter being placed into an auger hole.

A reducing connector 110, having an aperture 120 along a longitudinal, central axis that passes through the entire reducing connector 110, is secured to the bottom end 106 of the hollow tube 102. The reducing connector 110 reduces the width of the internal chamber 118 at the bottom end 106 of the hollow tube 102 to a narrower width that is about equal to the diameter of the second tube 114. The reducing connector 10 provides the means for maintaining the second tube 114 within the internal chamber 118 of the hollow tube 102, such that the second tube 114 slides within the aperture 120 of the reducing connector 110. When the second tube 114 is contained entirely or substantially within the internal chamber 118 of the hollow tube 102, the second tube 114 is in a retracted position, as shown in FIG. 1. When the second tube 114 is extended out of the internal chamber 118 of the hollow tube 102 such that the top end 122 of the second tube 114 is in proximity to the narrow (or bottom) end of the reducing connector 110, the second tube 114 is in an extended position, as shown in FIG. 2.

In the preferred embodiment, the internal chamber 118 has a diameter of about 3 inches whereas the length of the hollow tube 102 is about 18 inches. The second lube 114 has an outer diameter of about 1 and ½ inches and is also about 18 inches in length. The total length of the permeameter 100 in the retracted position is less than about 22 inches, with a preferred length in the retracted position of about 21 inches.

The second tube 114 is secured in the extended position by a compression fitting 112 attached to the reduced end of the reducing connector 110. In the preferred embodiment, the external surface of the reduced end of the reducing connector 110 is threaded such that a user simply screws on/off the compression fitting 112 to loosen and/or tighten the compression fitting 112 around the second tube 114. When the compression fitting 112 is tightened around the second tube 114, the second tube 114 is secured in place within the reducing connector 110. When the compression fitting 112 is loosened around the second tube 114, the second tube 114 is slidable within the reducing connector 110. In the preferred embodiment, the second tube 114 must slide loosely through the reducing connector 110 and the compression fitting 112 to prevent sand and soil grains from damaging the watertight seal created at the interface of the compression fitting 112 and the second tube 114.

A conventional measuring tape 116, having consecutive markings showing continuous ¼, ½, and 1 inch distances, is affixed to the outside surface of the hollow tube 102 such that the numbers extend vertically along the length, or longitudinal central axis, of the hollow tube 102. The lowest number, zero, of the measuring tape 116 is positioned at the bottom end 106 of the elongated tube 102 while the highest number of the measuring tape 116, as appropriate for the length of the hollow tube 102, is positioned at the top end 104 of the elongated tube 102.

In operation, as shown in FIG. 2, a user augers a 3 inch wide hole about 18 inches deep, auger hole 204, in the soil 202 using a conventional 2 and ¾ inch soil auger. This size auger hole 204 is recommended in the preferred embodiment to provide an accurate water level 214 in the auger hole 204 and to maintain better accuracy of test procedures, since experimentation has shown that the user in nearly all soil conditions deform the hole from 2 to 2 and ¾ inches to 3 inches. A deeper auger hole 204 can be dug to do testing at varying depths, but then either a longer second tube 114 or a longer hollow tube 102 than described above is needed to accommodate the deeper auger hole 204. The user extends the second tube 114 into the extended position and fills the internal chamber 118 of the hollow tube 102 with water via the bottom end 124 of the second tube 114 (with the stopper 126 removed) and creates a water line 212 in the hollow tube 102. Next, the user inverts the permeameter 100 and places the second tube 114 in the auger hole 204. In the preferred embodiment, the hollow tube 102 is made of clear plastic to allow the user easy access to view the water line 212. However, in an alternative embodiment, there may be one or more windows in the hollow tube 102 to provide the means for viewing the water line 212 within the hollow tube 102. In addition, the preferred embodiment of the second tube 114 is that it is made of metal or a comparable, hard and durable material that will support the permeameter 100 within an auger hole 204 and handle the pressure and damage that may result from the water and soil 202.

The second tube 114 also has a stopper 126 removably secured to its bottom end 124 to close off and seal the second tube 114. A user inserts the stopper 126 in the bottom end 124 of the second tube 114 before inversion of the permeameter 100 into the auger hole 204 during use of the permeameter 100, and removes the stopper 126 when the permeameter 100 is not in use, or when testing is complete, in order to quickly and efficiently remove any remaining water in the second tube 114 and the internal chamber 118. In the preferred embodiment, the stopper 126 is connected by a chain (not shown for convenience) to the inside of the second tube 114 to prevent the loss of the stopper 126 in the bottom 206 of the augered hole 204.

The second tube 114 also has an air hole 208 positioned at a pre-defined distance from the bottom end 124 of the second tube 114. The air hole 208 regulates the water level in the augered hole 204 in the soil 202 during use of the permeameter 100. In the preferred embodiment, the air hole 208 is about eight (8) inches from the bottom end 124.

The second tube 114 also has a slot 210 positioned between the bottom end 124 and the air hole 208. During use of the permeameter 100, water must flow through the slot 210 to get out of the second tube 114 because the bottom end 124 of the second tube 114 is closed off with the stopper 126. The water flows from the second tube 114 into the auger hole 204 via the slot 210, and ultimately, into the soil 202.

As water seeps from the auger hole 204 into the soil 202, the water in the auger hole 204 is replaced by water from the permeameter 100 to maintain a constant height, or water line 214, in the auger hole 204 of about 8 inches. The water line 214 in the auger hole 204 is determined by the location of the air hole 208 in the second tube 114.

Returning to the method for using the permeameter 100, after waiting a short time for the auger hole 204 to first fill with water and waiting for water flow from the permeameter 100 into the soil 202 to begin to stabilize (about 5 to 10 minutes after inserting the permeameter 100 into an auger hole 204), the user takes readings periodically from the measuring tape 116 on the hollow tube 102. That is, the user notes the duration of time from the beginning of the test (the time when water was first added to the permeameter 100 and the permeameter 100 was inserted into the auger hole 204), and the water level 212 in the internal chamber 118 of the hollow tube 102. Readings are taken regularly until at least two consecutive readings with a stabilized rate of fall is reached. A stabilized rate is when two or more consecutive readings (in minutes/inch in the preferred embodiment) are substantially the same. This stabilized rate indicates that the soil saturation has been reached, and an estimate on maximum hydraulic conductivity of the soil 202 can be made.

A table, as shown in Table 1 below, shows the correlation between the stabilized rate in minutes per inch with a corresponding design value in gallons per day per square feet for infiltration area require if the tested soil 202 is to be used to treat wastewater or storm water. That is, column 2 of Table 1 is the application rate, or the permeability of the soil 202 being tested with the safety multiplier, which in this case is 33%. This Table 1 includes an appropriate safety factor that is needed when designing an onsite system 300. For convenience, a copy of Table 1 may be affixed to the outside surface of the hollow tube 102.

TABLE 1

Soil Hydraulic Capacity

| Reading Fall Rate (minutes/inch) | Soil Hydraulic Capacity (gallons/day/sqft) |
| --- | --- |
| 0 to 5.8 | special instructions |
| 5.8 to 8.6 | 0.80 |
| 8.6 to 9.2 | 0.75 |
| 9.2 to 9.8 | 0.70 |
| 9.8 to 10.6 | 0.65 |
| 10.6 to 11.4 | 0.60 |
| 11.4 to 12.6 | 0.55 |
| 12.6 to 13.8 | 0.50 |
| 13.8 to 15 | 0.45 |
| 15 to 17 | .040 |
| 17 to 19.5 | 0.35 |
| 19.5 to 23 | 0.30 |
| 23 to 27 | 0.25 |
| 27 to 34 | 0.20 |
| 34 to 45 | 0.15 |
| 45 to 70 | 0.10 |
| 70 to 100 | 0.05 |

As noted in Table 1, when the reading fall rate is within the range 0 to 0.58 minutes/inch, the user must undertake special instructions because this fall rate indicates rapidly permeable soils. These special instructions are as follows: for treating wastewater and storm water, a soil hydraulic capacity value of 1.6 gallons/day/sqft should be used, and for a pressure dosed septic tank effluent, a soil hydraulic capacity value of 0.8 gallons/day/sqft should be used.

A user uses Table 1 to determine a soil infiltration area needed to treat a known amount of wastewater or storm water. Then, when designing a new onsite system 300, the user can allocate the appropriate amount of property. By way of example, if the amount of wastewater to be treated daily was 280 gallons/day, and the stabilized rate of saturation for the tested soil 202 was determined by the permeameter 100 and the above described test procedure as being 12 minutes/inch, than a soil infiltration area of 509 square feet is required for treating the 280 gallons/day wastewater. The infiltration area is calculated as follows: 280 gal/day divided by 0.55 gal/day/sqft=509 sq. ft.

A user also uses the permeameter 100 of the present invention to determine if additional water added to an existing onsite system 300 will be sure to leave the site 300 by remaining in the subsurface and not cause drainage or health hazards because of surfacing. In determining the maximum hydraulic conductivity of soil 202 between the water table line and the surface 302, the permeameter 100 should be used in combination with the following Table 2 wherein the second column is the permeability of the soil 202 being tested:

TABLE 2

Maximum soil hydraulic capacity

| Reading Fall Rate (minutes/inch) | Max. Soil Hydraulic Capacity (gallons/day/sqft) |
| --- | --- |
| 0 to 5.8 | 3.6 |
| 5.8 to 8.6 | 2.4 |
| 8.6 to 9.2 | 2.25 |
| 9.2 to 9.8 | 2.1 |
| 9.8 to 10.6 | 1.95 |
| 10.6 to 11.4 | 1.8 |
| 11.4 to 12.6 | 1.65 |
| 12.6 to 13.8 | 1.5 |
| 13.8 to 15 | 1.35 |
| 15 to 17 | 1.20 |
| 17 to 19.5 | 1.05 |
| 19.5 to 23 | 0.9 |
| 23 to 27 | 0.75 |
| 27 to 34 | 0.60 |
| 34 to 45 | 0.45 |
| 45 to 70 | 0.30 |
| 70 to 100 | 0.15 |
| 100 to 140 | 0.05 or 0.0 |
| 140+ | 0.0 |

For convenience, a copy of Table 2 may be affixed to the outside surface of the hollow tube 102.

B. Percolation Testing With a Permeameter

The permeameter 100 of the present invention is used to make a number of site design decisions pertaining to soil permeability and the treating of wastewater or storm water, including, but not limited to: (1) required bottom area of a trench; (2) the amount of water that each trench can accept given the site constraints; (3) how far apart the trenches should be once the loading of each trench is known; and (4) determining whether the calculated soil absorption system is acceptable for the actual site dimensions. The methods described hereto in no way reduces the need for proper evaluation of the many other factors involved in site evaluation of onsite systems for handling such wastewater and storm water. Such factors include but are not limited to: topography, soil texture, soil structure, seasonal high water table determinations, water use in the home, potential for nutrient loading on groundwater, geology of the area, etc. These factors must be considered whether designing a new onsite system or evaluating an existing onsite system.

In addition, soil percolation testing procedures, such as the permeameter 100, cannot be reliable if improper onsite system design, improper construction, or improper ongoing maintenance inspections of D-Boxes or other distribution methods allow unequal distribution of wastewater to different trenches. If the site's hydraulic capacity/trench capacities are marginal, guarantees of equal distribution should be built into onsite system designs, such as: (1) absolutely level trenches along contours, and (2) use of siphons and pumps.

Figure 3:
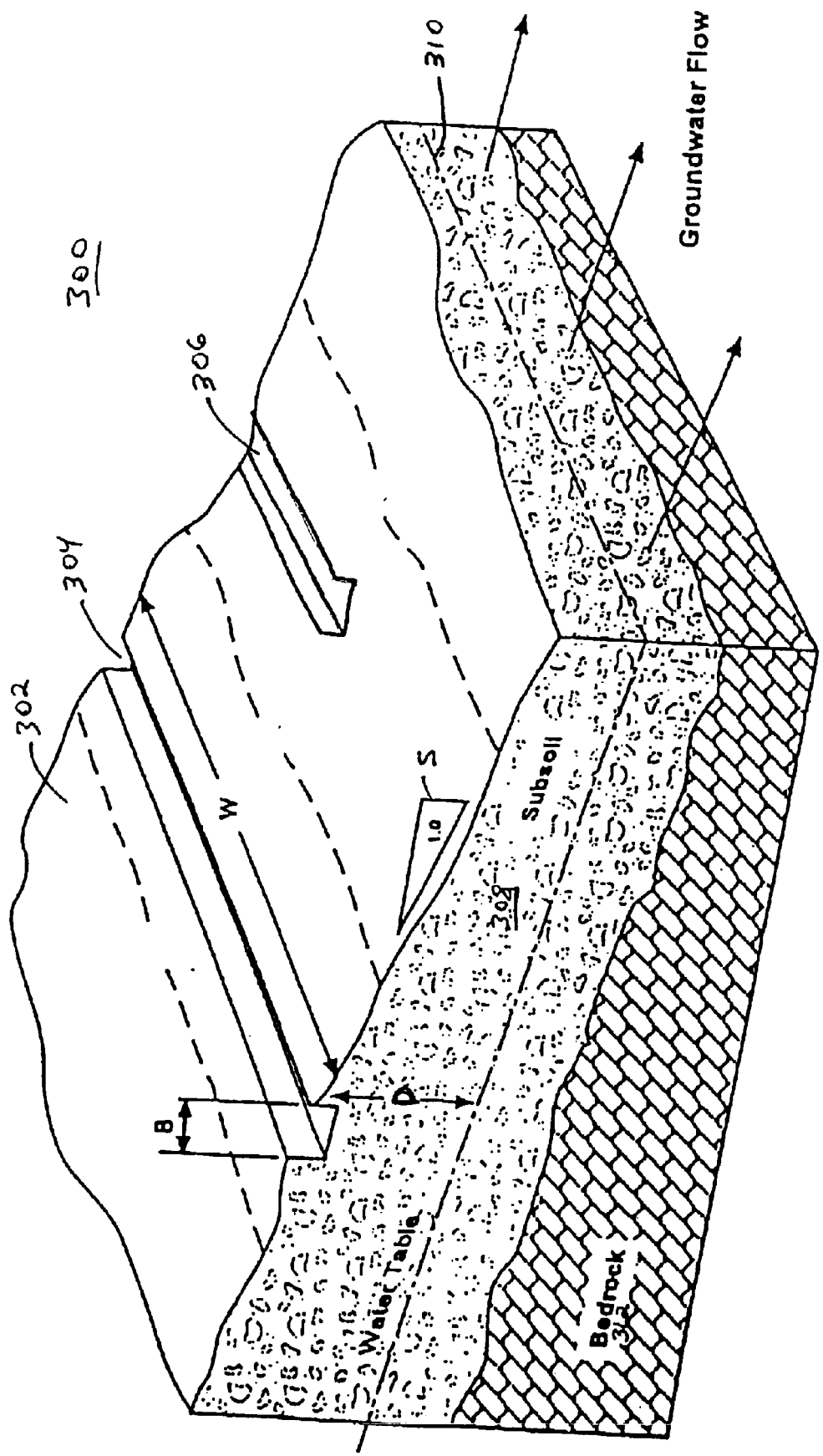
FIG. 3 is a perspective view showing an exemplary onsite system for treating wastewater and storm water.
Figure 4:
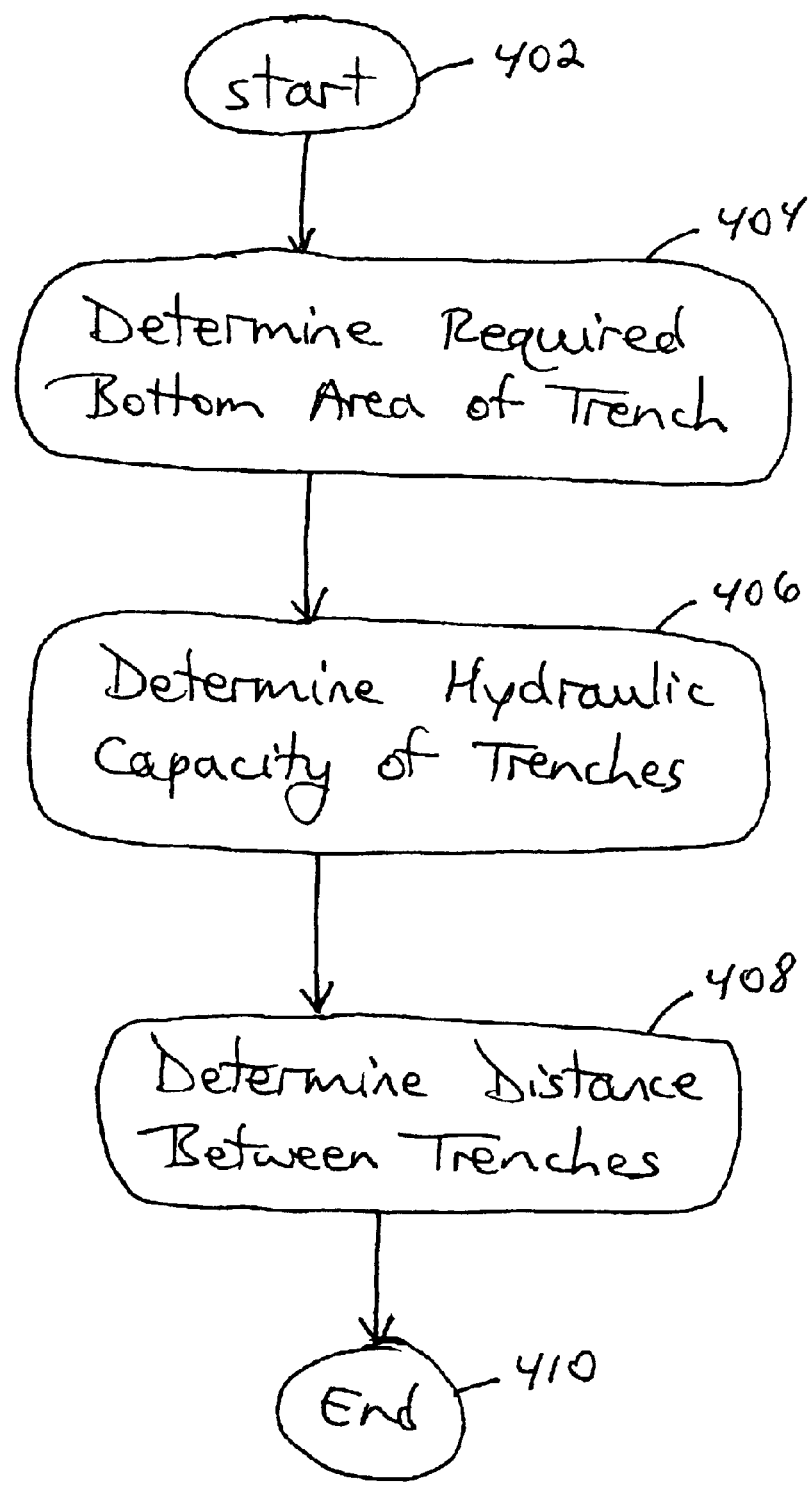
FIG. 4 is a block diagram illustrating the process for evaluation and designing an onsite system for treating wastewater and storm water.

FIGS. 4–8 are block diagrams for illustrating the preferred method for evaluating and designing onsite systems for treating wastewater and storm water. These processes are described in reference to FIG. 3 is a perspective view showing an exemplary onsite system 300 for treating wastewater and storm water. In FIG. 4, processing begins at step 402 and immediately proceeds to step 404 where the user determines the required bottom area of one or more trenches 304, 306 to be used in the onsite system 300. The processing of step 402 is described in greater detail below. After determining the bottom area for the trenches 304, 306, the user proceeds to step 404 to determine the hydraulic capacity of each trench 304, 306. The processing of step 404 is described in greater detail below. The user next continues to step 408 to determine the distance between the trenches 304, 306, and is also described in greater detail below. Once the onsite system 300 is evaluated and/or designed, the user finishes at step 410.

Figure 5:
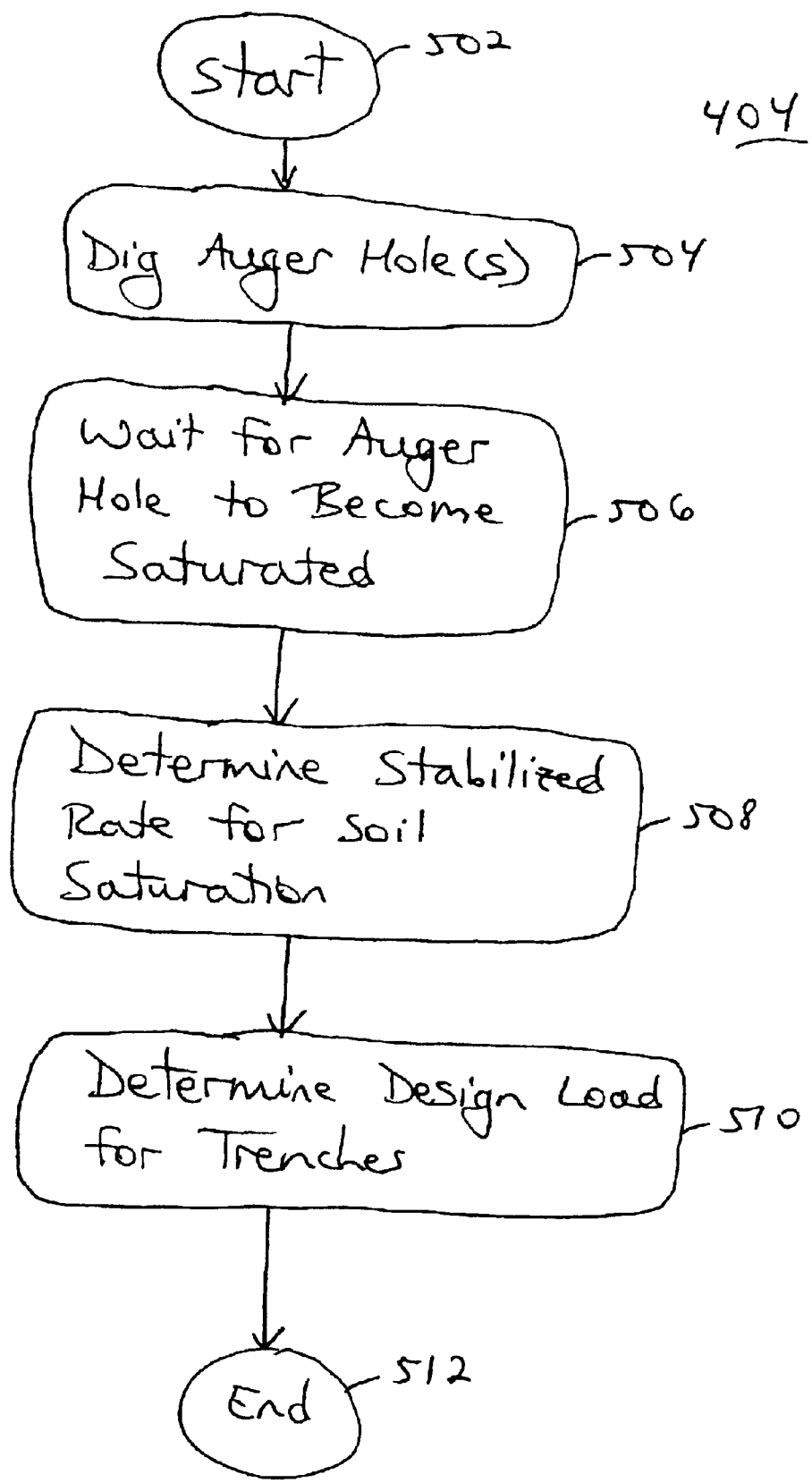
FIG. 5 is a block diagram illustrating the process for determining the required bottom area of a trench.

Referring again to step 404, the process of determining the bottom area of each trench 304, 306 is shown in FIG. 5. Processing starts at step 502 and immediately continues to step 504. In step 504, the user determines where to auger holes for the pereameter 100 analysis based on a visual survey of the onsite system 300. Preferably, the user makes several auger holes 204 in the onsite system 300 for testing purposes, including testing those areas where a trench 304, 306 may be located. In the preferred embodiment, the user augers three to four 4 feet deep test holes for soil texture analysis. The user then augers one to three holes, auger holes 204, to a depth equal to about the length of the permeameter 100, about 2 feet deep. Optionally, the user scratches the inside of each auger hole 204 with a steel brush or stick with nails protruding to prevent smearing. In particular, this should be done in soils with high clay content. The user extends the second tube 114 of the permeameter 100 to the extended position, fills the internal chamber 118 of the hollow tube 102 of the permeameter 100 with water, inverts the permeameter 100, and inserts the second tube 114 in the auger hole 204. The user then continues to step 506 to wait for the auger hole 204 to become saturated by the water flowing out of the permeameter 100. This should take about 5 to 10 minutes.

Figure 6:
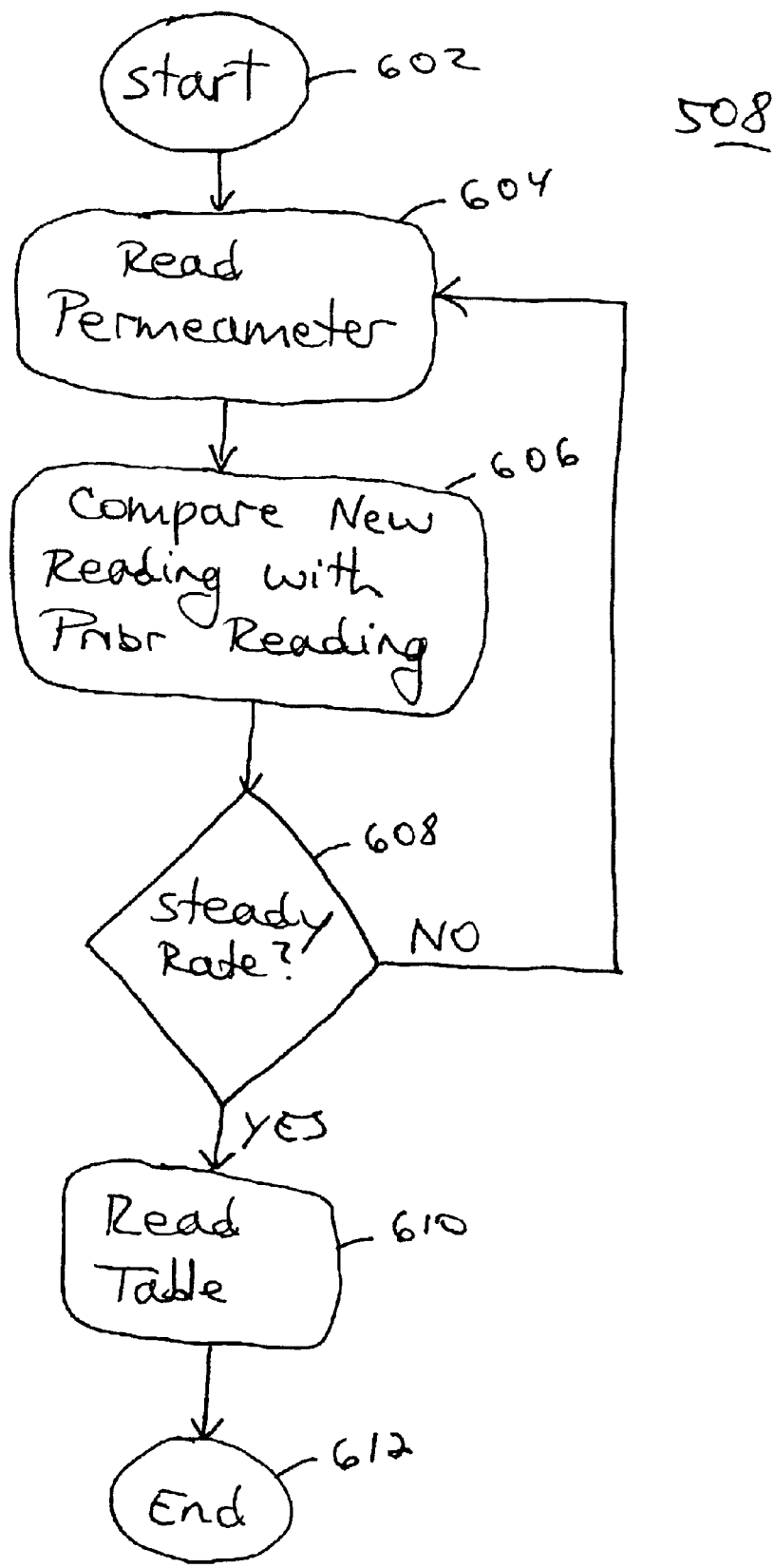
FIG. 6 is a block diagram illustrating the process for determining the stabilized rate for soil saturation.
Figure 7:
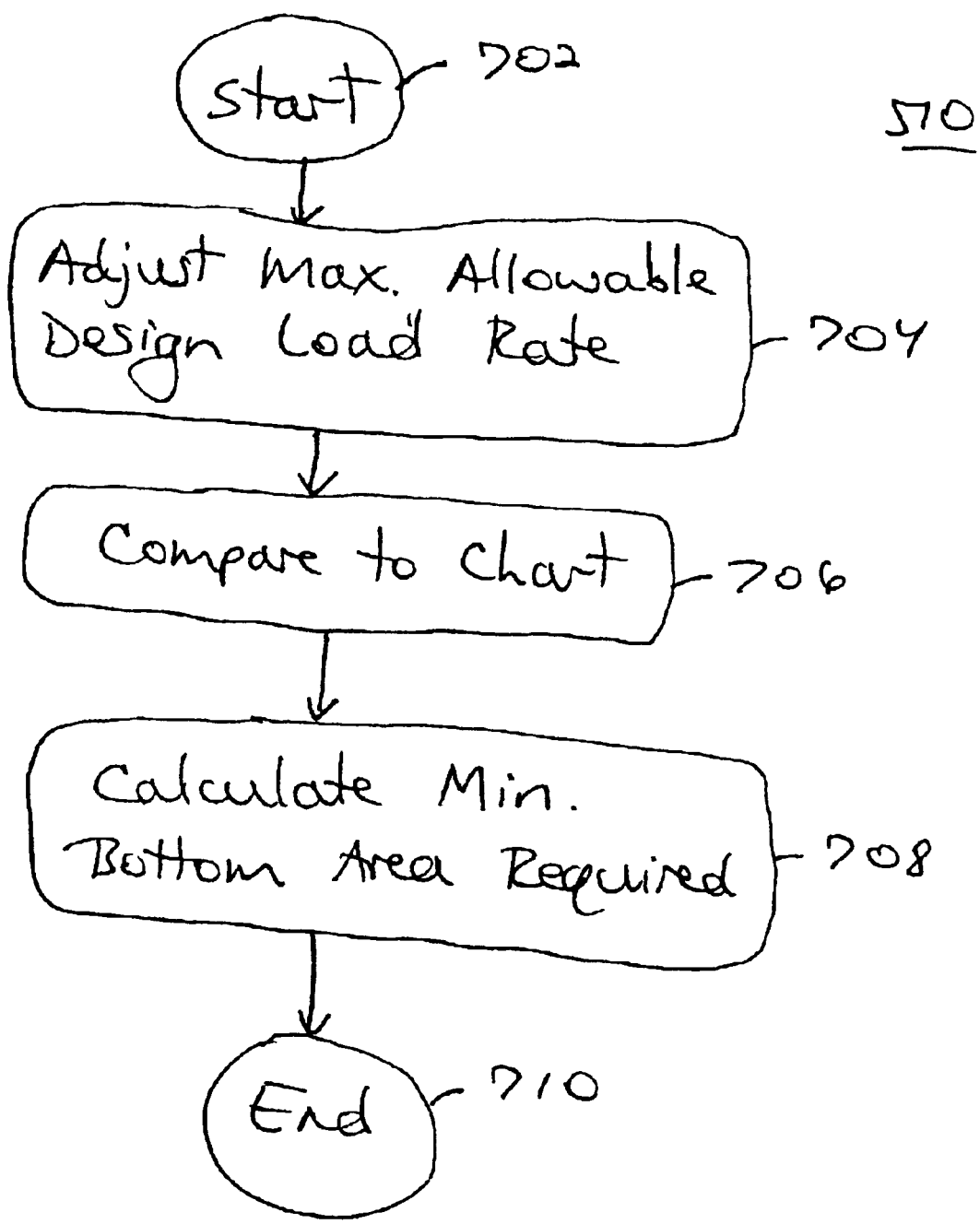
FIG. 7 is a block diagram illustrating the process for determining a design load for a trench.

Once the auger hole 204 is saturated, the user continues to step 508 and determines the stabilized rate for soil 202 saturation. This step 508 is shown in FIG. 6 and is also described above. Processing begins at step 602 and immediately proceeds to step 604. In step 604, the user takes a reading from the measuring tape 116 on the hollow tube 102 every 5–7 minutes for at least 20 minutes. For each reading, the user calculates the fall in the height of the water level 212 in the internal chamber 118 of the hollow tube 102 from the prior reading. Continuing to step 606, the user compares the new reading with the prior reading and determines whether the minutes per inch rate of fall is consistent or steady for each reading period. In step 608, the user determines whether a steady rate of fall exists. A steady rate of fall exists when two or more consecutive readings (rate of fall of the water level 212) are equal or substantially equal, e.g., within plus or minus 0.5 minutes/inch in the preferred embodiment. If a steady rate does not exist, processing returns to step 604 and another reading of the measuring tape 116 takes place at an appropriate interval from the last reading.

Returning to step 608, if a steady rate exists, processing continues to step 610. In step 610, the user reads Table 2 by locating in the first column the stabilized rate of fall of the water level 212. When the entry in the first column of Table 2 is located, the user finds the corresponding maximum allowable design loading rate (MDLR SOIL) for the soil 202 being tested in the second column. If the rate of fall of the waterline 212 does not stabilize, the user must either continue the test until it does, or if the soil 202 is rapidly permeable, the user should choose the MDLR SOIL for the last set of readings taken before the permeameter 100 is empty of water.

Once the MDLR SOIL is determined, the user continues to step 612 at which processing returns to FIG. 5 and step 510 in which the user determines the design load for the trenches 304, 306. Step 510 is described in greater detail in FIG. 7 wherein processing begins at step 702 and immediately proceeds to step 704. In step 704, the user adjusts the MDLR SOIL downwards by multiplying it by 33%, thereby calculating the DLR Trench. The downward multiplier of 33% is chosen for convenience purpose only in that it is based on the inventors' experience. Alternative downward multiplier values can also be used. This downward adjustment provides the means for taking into account unusually wet rainfalls and an error factor in testing with the permeameter 100, and also ensures partially saturated soil conditions for oxygen transfer to take place which are needed for soil organisms to adequately treat the wastewater in soil 202.

After the DLR Trench is calculated, processing continues to step 706 in which the DLR Trench is compared to the following chart: 0.8 gal/day/sqft (septic systems), and 1.6 gal/day/sqft (aerobic systems). The user uses the lower value to size the bottom area of the trench 304, 306 for the onsite system 300. Once the lower value is found, the user uses it in step 708 to calculate the minimum bottom area required for a trench 304, 306. An example of this processing is shown below:

Example: onsite septic system for a 3 bedroom home

Permeameter testing of 13 min/inch shows a MDLR SOIL=1.5 gal/day/sqft (Table 2)

Thus, DLR Trench=1.5*33%=0.5 gal/day/sqft (Table 1 entry)

Compare to chart: Use 0.5 because 0.5<0.8 (use 0.8 because septic system)

Result: Design flow for a 3 bedroom home in West Virginia is 280 gal/day.

Therefore, the Bottom Area required for a trench is 280/0.5=560 sqft.

This represents the absolute minimum bottom area of a trench 304, 306, such that no adjustments below this square footage is permitted. A 2-inch sand layer is recommended in the bottom of all trenches 304, 306.

Figure 8:
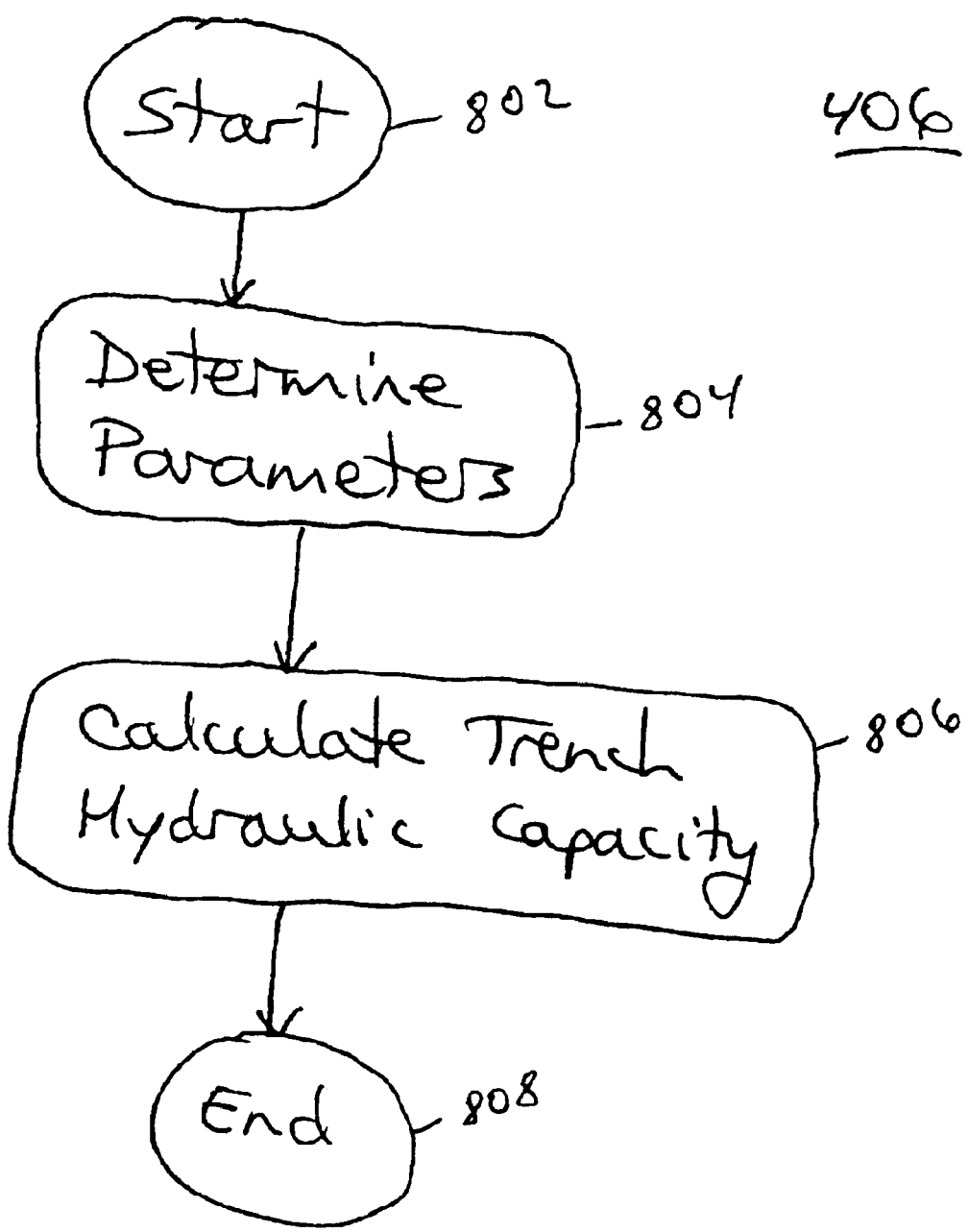
FIG. 8 is a block diagram illustrating the process for determining the hydraulic capacity for trenches.

Once the bottom area is calculated, processing continues to step 710 and returns to FIG. 5 and step 512. In step 512, processing in turn returns to FIG. 4 and proceeds to step 406. In step 406, the user determines the hydraulic capacity of the trenches 304, 306, and is shown in greater detail in FIG. 8. In FIG. 8, processing begins at step 802 and immediately continues to step 804. In step 804, the user collects information on certain, needed parameters whenever the slope "S" of the onsite system 300 is greater than 5%. The needed parameters are:

1. MDLR SOIL: The quantity of water that can move through the soil under saturated conditions and is determined using the permeameter 100 and the process of step 508.
2. Width "W" of the onsite system 300: This is a property dimension in feet along the surface 302 or contour of the real property usable as a drainfield for the onsite system 300. It follows the contours of the onsite system 300. The width W is important because the evaluation assumes that an elevation in groundwater will be caused by adding water to the onsite system 300 which may affect downslope drainfield areas adversely.
3. Usable Depth "D" of subsoil 308: This is the dimension in feet of the limiting layer of the subsoil 308 for the onsite system 300 which can be used for a drainfield for the wastewater. This dimension does not include the following: seasonable high water, impermeable clay, impermeable bedrock 312, or groundwater. Note that permeable bedrocks are included in this dimension. Therefore, karst geology may make this usable depth D a very large number if this data is available for the onsite system 300.
4. Slope "S" of the onsite system 300: The slope S is estimated as a percentage converted to decimal form for calculations (ex. 12% slope S=0.12) and represents the slope S of the onsite system 300 available as a drainfield area. Slope S is important because as the slope S increases, hydraulic gradient increases; thus, gravity will push the wastewater through the soil 202 laterally at a more rapid rate as the slope S increases. If vertical flow under a proposed trench 304, 306 site can be confirmed, such as in permeable bedrock conditions, with a permeability greater than the soil 202 tested at the surface 302, this slope S can be estimated at 50% (0.5) to 100% (1.0) since the flow out of the drainfield will be vertical and not lateral down the slope S.

Given these parameters, the user estimates the maximum wastewater a trench 304, 306 along the width W of the slope S can accept. That is, processing continues to step 806 to determine the hydraulic capacity of the trench 306, 308. For example, a narrow width W, shallow usable depth S of subsoil 308, and gradual slopes S are all more likely to make an onsite system 300 "hydraulically" unsuitable given the same soil permeability. By contrast, the same narrow width W onsite system 300, with deeper D subsoil 308 and a significant slope S of 20% may be hydraulically suitable. Each onsite system 300 situation is different, but these are the key parameters for estimating the likelihood of a soil absorption system failure.

In step 806, the user calculates the maximum water a given length of trench 304, 306 can accept under saturated soil conditions in gal/day. The calculation is as follows:

Trench Hydraulic Capacity ($THC$)=MDLR SOIL*Width W*usable Depth $D$*Slope $S$

See the following examples:

Sample Site 1:

onsite system for 3 bedroom home has clay layer at 3 and ½ feet, a slope of 12% and 100 feet of Width W available along the contour of the slope S.

Permeameter readings indicate a fall of 13 min/inch (see above for=1.5 gal/day/sqft).

Therefore, THC=1.5 gal/day/sqft*100 ft*3.5 ft*0.12=63 gal/day

The number of trenches required=280 gal/day divided by 63 gal/day=4.4 trenches or 440 feet of trench.

The width of the trenches is based on DLR Trench:

Bottom Area required was 560 sqft (see above example)

Thus, width of trench = total bottom area divided by total trench length
= 560/440 = 1.27 ft (or at least 16 inches wide)

Sample Site 2:

onsite system for 3 bedroom home (having a flow of 280 gal/day and a calculated soil infiltration area requirement of 509 sqft) has clay layer at 3 feet, a slope of 10% and 100 feet of Width W available along the contour of the slope S.

Permeameter readings indicate a fall of 12 min/inch (Table 2=1.65 gal/day/sqft).

Therefore, THC=1.65 gal/day/sqft*100 ft*3 ft*0.10=49 gal/day

The number of trenches required=280 gal/day divided by 49 gal/day=5.7 trenches or 571 feet of trench.

The width of the trenches is based on DLR Trench:

Bottom Area required is 518 sqft (1.65*33%<0.8, so use 0.54; 280/0.54=518)

Thus, width of trench = total bottom area divided by total trench length
= 518/571 = 0.9 ft (or about 1 foot wide)

After the trench hydraulic capacity is calculated in step 806, the processing continues to step 808 where it returns to FIG. 4 and step 408. In step 408, the user determines the distance between the trenches 304, 306. To calculate this distance, one could use state regulations, such as in West Virginia, there is a minimum six feet separation required between trenches 304, 306. However, under certain conditions, the state minimum could create a failure due to wastewater mounding under the onsite system 300. Therefore, to calculate trench 304, 306 separation:

Trench Separation $TS=THC/$(Width $W$*limiting layer expected permeability $LLP$)

It is important to note that permeability of most clay layers is estimated at 0.05 gal/day/sqft. This is a very slow permeability and this value can be changed if more accurate soil evaluation can be done on the limited layer.

Sample Site 1 Continued:

Continuing the previous Sample Site 1, how far downslope before the 68 gallons applied to the trench is absorbed? TS=68/(100*0.05)=13.6 feet downslope for the next trench.

Sample Site 2 Continued:

Continuing the previous Sample Site 2, the TS=49/(100*0.05)=9.8 feet between trenches C. Calibration of Permeameter The permeameter 100 of the present invention is not limited to the sizes and dimensions as disclosed herein. These dimensions are provided for convenience purpose only. However, it is important to note that the values shown in the second column of both Table 1 and Table 2 are dependent on the dimensions of the permeameter 100, the dimensions of the auger hole 204, and the depth of the water (the water line 214) in the auger hole 204. Therefore, if a permeameter 100 of the present invention is made using different dimensions, or a different sized auger hole 204 and/or water line 214 in the auger hole 204 is used, than those disclosed as the preferred embodiment, the values of the second columns of Table 1 and Table 2 must be recalculated.

The second columns of Table 1 and Table 2 are calculated using the formulas shown on FIGS. 9 and 10. These formulas use standard soil absorption principles while taking advantage of the variable dimensions of the permeameter 100, the auger hole 204, and the water level 214 in the auger hole 204. Specifically, the formulas are shown in detail in FIG. 10, while FIG. 9 shows an application of those formulas to the dimensions used herein as the preferred embodiment along with a reading fall rate of 8 minutes, 45 seconds (which equals 8.75 minutes). Once the values are input into the formulas, the second column of Table 1 is calculated using the formula contained in cell F14 of FIG. 10, while the second column of Table 2 is calculated using the formula contained in cell F11 of FIG. 10. According to FIG. 9, the Table 1 entry is 0.82 gal/day/sqft and the entry in Table 2 is 2.4 gal/day/sqft.

Reviewing FIG. 9 table entries with those of Table 1 and Table 2, it is readily apparent that an additional factoring has occurred. That is, for a reading fall rate of 8.75 minutes/inch, Table 1 has an entry of 0.75 gal/day/sqft and Table 2 has an entry of 2.25 gal/day/sqft. Comparing the actual entries in Table 1 and Table 2 with the values contained in FIG. 9, it is readily apparent that the preferred embodiment of calculating the entries for Table 1 and Table 2 approximates the actual values of the reading fall rate. That is, the first column of Table 1 and Table 2 contains ranges of multiple reading fall rates. Therefore, the corresponding entry in the second column of these tables must take all of the hydraulic capacities for each entry in a given range and approximate it into a single value. In addition, the entries of the second column of Table 1 includes an additional safety factor (or margin of error) to ensure a very conservative approach for evaluating and designing onsite systems 300. It would be readily apparent to one of ordinary skill in the relevant art to use a conventional safety factoring scheme, or to apply an appropriate error of margin, to the calculation of the values in the second column of Table 1 and Table 2.

CONCLUSION

While various embodiments of the present invention have been described above, it should be under-stood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for evaluating soil having a stabilized rate of soil saturation and designing an onsite system having one or more trenches for treating wastewater and storm water, each trench having with a bottom area, an hydraulic capacity, and a design load, and each trench being spaced apart from the other trenches a pre-defined distance, comprising the steps of:
   (a) determining a required bottom area of the trenches;
   (b) determining a hydraulic capacity of the trenches; and
   (c) determining a required distance between the trenches.

2. The method of claim 1, wherein said step (a) comprises the following steps:
   (a1) augering one or more holes in the onsite system;
   (a2) saturating said one or more holes of said step (a1) using a permeameter;
   (a3) determining a stabilized rate of soil saturation;
   (a4) determining a design load rate for the soil using said stabilized rate of soil saturation;
   (a5) multiplying said design load rate for the soil from step (a4) by a predefined error factor, thereby generating a design load for said trenches; and
   (a6) dividing a predefined standard design flow for the onsite system by said design load rate for trenches, thereby generating said required bottom area of the trenches.

3. The method of claim 2, wherein said predefined error factor of said step (a5) is between about 0.30 and about 0.40.

4. The method of claim 3, wherein said predefined error factor is about 0.33.

5. The method of claim 1, wherein said step (b) comprises:
   (b1) collecting information on parameters including MDLR SOIL, width of the onsite system, depth of usable soil, and slope of the onsite system;
   (b2) multiplying MDLR SOIL, width of onsite system, depth of usable soil, and slope of the onsite system, thereby generating said hydraulic capacity of the trenches;
   (b3) determining a number of trenches needed for the onsite system, said number of trenches calculated by dividing a predefined standard design flow for the onsite system by said hydraulic capacity of the trenches; and
   (b4) determining a width of the trenches by dividing said required bottom area of the trenches by (said number of trenches multipled by the width of the onsite system).

6. The method of claim 2, wherein said pemeameter comprises:
   a hollow tube having a top end, a bottom end, a diameter, an outer surface, and an internal chamber having a width;
   a means for sealing said top end of said hollow tube;
   a second tube having a top end, a bottom end, a diameter, a means for closing and sealing said bottom end of said second tube, an air hole positioned at a pre-defined distance from said bottom end, and a slot positioned between said bottom end and said air hole, wherein said diameter of said second tube is less than said diameter of said hollow tube such that said second tube is slidably housed within said internal chamber of said hollow tube and is adapted to move between a retracted position and an extended position in relation to said hollow tube; and
   a means for slidably maintaining said second tube within said internal chamber of said hollow tube.

7. The method of claim 6, wherein said step (a2) comprises the steps of:
   (a2i) extending said second tube of said permeameter to said extended position;
   (a2ii) inverting said permeameter such that said second tube is extended downward;
   (a2iii) filling said permeameter with water; and
   (a2iv) inserting said permeameter into one said hole of said step (a1) such that said bottom end of said second tube is in a bottom of said hole.

8. The method of claim 7, wherein said step (a3) comprises the steps of:
   (a3i) making a first reading of a fall rate of water within said hollow tube;
   (a3ii) making a second reading of a fall rate of water within said hollow tube at a predefined duration of time from performing step (a3i);
   (a3iii) making subsequent readings of a fall rate of water within said hollow tube at the predefined duration of time;
   (a3iv) determining whether two consecutive readings of a fall rate are substantially equal; and
   (a3v) if said two consecutive readings of a fall rate are substantially equal in step (a3iv), setting said stabilized rate of soil saturation as said two consecutive readings of a fall rate.

9. The method of claim 5, wherein said MDLR SOIL for the soil surrounding said hole is calculated using the following mathematical formula: $J7*(LN(J8+J9)-1)/J10$;
   wherein J7 is calculated using the following mathematical formula: $(((D5)^2*pi*7.4939)/(4*1728))/((D8*60+F8)/86400)$;
   wherein J8 is calculated using the following mathematical formula: $D6/(D7/2)$;
   wherein J9 is calculated using the following mathematical formula: $SQRT(J8^2-1)$;
   wherein J10 is calculated using the following mathematical formula: $2*pi*E6^2$;

wherein D5 is a diameter of a reservoir in inches;

wherein D8 is a time to fall one inch in minutes;

wherein F8 is a time to fall one inch in seconds;

wherein D6 is a depth of water in said hole in inches;

wherein D7 is a diameter of said hole in inches; and wherein E6 is a depth of water in said hole in inches divided by 12.

10. The method of claim 5, wherein said step (c) comprises the step of:

(c1) dividing said hydraulic capacity of the trenches by (the width of the onsite system multiplied by the limiting layer expected permeability LLP).

11. A method for determining a soil infiltration area needed to treat a known amount of wastewater, comprising the steps of:

(a) determining an amount of wastewater to be treated daily;

(b) determining a stabilized rate of saturation of an area of soil;

(c) determining a soil hydraulic capacity that corresponds with said stabilized rate of saturation according to the following predefined rates:

| Reading Fall Rate (minutes/inch) | Soil Hydraulic Capacity (gallons/day/sqft) |
| --- | --- |
| 0 to 5.8 | about 0.8 to about 1.6 |
| 5.8 to 8.6 | 0.80 |
| 8.6 to 9.2 | 0.75 |
| 9.2 to 9.8 | 0.70 |
| 9.8 to 10.6 | 0.65 |
| 10.6 to 11.4 | 0.60 |
| 11.4 to 12.6 | 0.55 |
| 12.6 to 13.8 | 0.50 |
| 13.8 to 15 | 0.45 |
| 15 to 17 | .040 |
| 17 to 19.5 | 0.35 |
| 19.5 to 23 | 0.30 |
| 23 to 27 | 0.25 |
| 27 to 34 | 0.20 |
| 34 to 45 | 0.15 |
| 45 to 70 | 0.10 |
| 70 to 100 | 0.05 | and (d) dividing said amount of wastewater to be treated daily by said soil hydraulic capacity.

12. The method of claim 11, wherein said step (b) comprises the step of using a permeameter for determining said stabilized rate of saturation of the area of soil, wherein said permeameter comprises:

a hollow tube having a top end, a bottom end, a diameter, an outer surface, and an internal chamber having a width;

a means for sealing said top end of said hollow tube;

a second tube having a top end, a bottom end, a diameter, a means for closing and sealing said bottom end of said second tube, an air hole positioned at a pre-defined distance from said bottom end, and a slot positioned between said bottom end and said air hole, wherein said diameter of said second tube is less than said diameter of said hollow tube such that said second tube is slidably housed within said internal chamber of said hollow tube and is adapted to move between a retracted position and an extended position in relation to said hollow tube; and a means for slidably maintaining said second tube within said internal chamber of said hollow tube.

13. The method of claim 12, wherein said step (b) further comprises:

(b1) augering a hole in the area of soil;

(b2) extending said second tube of said permeameter to an extended position;

(b3) inverting said permeameter such that said second tube is extended downward;

(b4) filling said hollow tube of said permeameter with water;

(b5) inserting said permeameter into the hole of said step (b1) such that said bottom end of said second tube is in a bottom of the hole;

(b6) determining whether a stable reading fall rate has been reached for the hole of step (b1); and (b7) once a stable reading fall rate has been reached in said step (b6), setting said stable reading fall rate as said stabilized rate of saturation of the area of soil.

14. The method of claim 12, wherein said soil hydraulic capacity is calculated using the following mathematical formula: $(J7*(LN(J8+J9)-1)/J10)*0.5*0.666667$;

wherein J7 is calculated using the following mathematical formula: $(((D5)^2*pi*7.4939)/(4*1728))/((D8*60+F8)/86400)$;

wherein J8 is calculated using the following mathematical formula: $D6/(D7/2)$;

wherein J9 is calculated using the following mathematical formula: $SQRT(J8^2-1)$;

wherein J10 is calculated using the following mathematical formula: $2*pi*E6^2$;

wherein D5 is a diameter of said internal chamber of said hollow tube in inches;

wherein D8 is a time to fall one inch in minutes;

wherein F8 is a time to fall one inch in seconds;

wherein D6 is a depth of water in the hole in inches;

wherein D7 is a diameter of the hole in inches; and wherein E6 is a depth of water in the hole in inches divided by 12.

15. The method of claim 13, wherein said step (b6) comprises the steps of:

(b6i) making a first reading of a fall rate of water within said hollow tube;

(b6ii) making a second reading of a fall rate of water within said hollow tube at a predefined duration of time from performing step (b6i);

(b6iii) making subsequent readings of a fall rate of water within said hollow tube at the predefined duration of time;

(b6iv) determining whether two consecutive readings of a fall rate are substantially equal; and (b6v) if said two consecutive readings of a fall rate are substantially equal in step (b6iv), setting said stable reading fall rate as said two consecutive readings of a fall rate.

16. A method for calculating a soil hydraulic capability for an area of soil, comprising the steps of:

(a) determining a stabilized rate of saturation of the area of soil;

(b) determining a soil hydraulic capacity that corresponds with said stabilized rate of saturation according to the following predefined rates:

| Reading Fall Rate (minutes/inch) | Soil Hydraulic Capacity (gallons/day/sqft) |
|---|---|
| 0 to 5.8 | about 0.8 to about 1.6 |
| 5.8 to 8.6 | 0.80 |
| 8.6 to 9.2 | 0.75 |
| 9.2 to 9.8 | 0.70 |
| 9.8 to 10.6 | 0.65 |
| 10.6 to 11.4 | 0.60 |
| 11.4 to 12.6 | 0.55 |
| 12.6 to 13.8 | 0.50 |
| 13.8 to 15 | 0.45 |
| 15 to 17 | .040 |
| 17 to 19.5 | 0.35 |
| 19.5 to 23 | 0.30 |
| 23 to 27 | 0.25 |
| 27 to 34 | 0.20 |
| 34 to 45 | 0.15 |
| 45 to 70 | 0.10 |
| 70 to 100 | 0.05 |

17. The method of claim 16, wherein said soil hydraulic capacity is calculated using the following mathematical formula: $(J7*(LN(J8+J9)-1)/J10)*0.5*0.666667$;

wherein J7 is calculated using the following mathematical formula: $((D5)^2*pi*7.4939)/(4*1728))/((D8*60+F8)/86400)$;

wherein J8 is calculated using the following mathematical formula: $D6/(D7/2)$;

wherein J9 is calculated using the following mathematical formula: $SQRT(J8^2-1)$;

wherein J10 is calculated using the following mathematical formula: $2*pi*E6^2$;

wherein D5 is a diameter of a reservoir in inches;

wherein D8 is a time to fall one inch in minutes;

wherein F8 is a time to fall one inch in seconds;

wherein D6 is a depth of water in the hole in inches;

wherein D7 is a diameter of the hole in inches; and wherein E6 is a depth of water in the hole in inches divided by 12.

18. The method of claim 16, wherein said step (a) comprises the step of using a permeameter for determining said stabilized rate of saturation of the area of soil, wherein said permeameter comprises:

a hollow tube having a top end, a bottom end, a diameter, an outer surface, and an internal chamber having a width;

a means for sealing said top end of said hollow tube;

a second tube having a top end, a bottom end, a diameter, a means for closing and sealing said bottom end of said second tube, an air hole positioned at a pre-defined distance from said bottom end, and a slot positioned between said bottom end and said air hole, wherein said diameter of said second tube is less than said diameter of said hollow tube such that said second tube is slidably housed within said internal chamber of said hollow tube and is adapted to move between a retracted position and an extended position in relation to said hollow tube; and a means for slidably maintaining said second tube within said internal chamber of said hollow tube.

19. The method of claim 18, wherein said step (a) further comprises the steps of:

(a1) angering a hole in the area of soil;

(a2) extending said second tube of said permeameter to an extended position;

(a3) inverting said permeameter such that said second tube is extended downward;

(a4) filling said hollow tube of said permeameter with water, (a5) inserting said permeameter into the hole of said step (a1) such that said bottom end of said second tube is in a bottom of the hole;

(a6) determining whether a stable reading fall rate has been reached for the hole of step (a1); and (a7) once a stable reading fall rate has been reached in said step (a6), setting said stable reading fall rate as said stabilized rate of saturation of the area of soil.

20. The method of claim 19, wherein said step (a6) comprises the steps of:

(a6i) making a first reading of a fall rate of water within said hollow tube;

(a6ii) making a second reading of a fall rate of water within said hollow tube at a predefined duration of time from performing step (a6i);

(a6iii) making subsequent readings of a fall rate of water within said hollow tube at the predefined duration of time;

(a6iv) determining whether two consecutive readings of a fall rate are substantially equal; and (a6v) if said two consecutive readings of a fall rate are substantially equal in step (a6iv), setting said stable reading fall rate as said two consecutive readings of a fall rate.

21. A method for determining a maximum hydraulic conductivity of soil, comprising the steps of:

(a) determining a stabilized rate of saturation of an area of soil;

(b) determining a maximum hydraulic conductivity of the area of soil that corresponds with said stabilized rate of saturation according to the following predefined rates:

| Reading Fall Rate (minutes/inch) | Max. Soil Hydraulic Capacity (gallons/day/sqft) |
|---|---|
| 0 to 5.8 | 3.6 |
| 5.8 to 8.6 | 2.4 |
| 8.6 to 9.2 | 2.25 |
| 9.2 to 9.8 | 2.1 |
| 9.8 to 10.6 | 1.95 |
| 10.6 to 11.4 | 1.8 |
| 11.4 to 12.6 | 1.65 |
| 12.6 to 13.8 | 1.5 |
| 13.8 to 15 | 1.35 |
| 15 to 17 | 1.20 |
| 17 to 19.5 | 1.05 |
| 19.5 to 23 | 0.9 |
| 23 to 27 | 0.75 |
| 27 to 34 | 0.60 |
| 34 to 45 | 0.45 |
| 45 to 70 | 0.30 |
| 70 to 100 | 0.15 |
| 100 to 140 | 0.05 or 0.0 |
| 140+ | 0.0 |

22. The method of claim 21 wherein said maximum hydraulic conductivity is calculated using the following mathematical formula: $J7*(LN(J8+J9)-1)/J10$;

wherein J7 is calculated using the following mathematical formula: $(((D5)^2*pi*7.4939)/(4*1728))/((D8*60+F8)/86400)$;

wherein J8 is calculated using the following mathematical formula: $D6/(D7/2)$;

wherein J9 is calculated using the following mathematical formula: SQRT(J8^2−1);

wherein J10 is calculated using the following mathematical formula: 2*pi*E6^2;

wherein D5 is a diameter of a reservoir in inches;

wherein D8 is a time to fall one inch in minutes;

wherein F8 is a time to fall one inch in seconds;

wherein D6 is a depth of water in said hole in inches;

wherein D7 is a diameter of said hole in inches; and wherein E6 is a depth of water in said hole in inches divided by 12.

23. The method of claim 21, wherein said step (a) comprises the step of using a permeameter for determining said stabilized rate of saturation of the area of soil, wherein said permeameter comprises:

a hollow tube having a top end, a bottom end, a diameter, an outer surface, and an internal chamber having a width;

a means for sealing said top end of said hollow tube;

a second tube having a top end, a bottom end, a diameter, a means for closing and sealing said bottom end of said second tube, an air hole positioned at a pre-defined distance from said bottom end, and a slot positioned between said bottom end and said air hole, wherein said diameter of said second tube is less than said diameter of said hollow tube such that said second tube is slidably housed within said internal chamber of said hollow tube and is adapted to move between a retracted position and an extended position in relation to said hollow tube; and a means for slidably maintaining said second tube within said internal chamber of said hollow tube.

24. The method of claim 23, wherein said step (a) further comprises the steps of:

(a1) augering a hole in the area of soil;

(a2) extending said second tube of said permeameter to an extended position;

(a3) inverting said permeameter such that said second tube is extended downward;

(a4) filling said hollow tube of said permeameter with water;

(a5) inserting said permeameter into the hole of said step (a1) such that said bottom end of said second tube is in a bottom of the hole;

(a6) determining whether a stable reading fall rate has been reached for the hole of step (a1); and (a7) once a stable reading fall rate has been reached in said step (a6), setting said stable reading fall rate as said stabilized rate of saturation of the area of soil.

25. The method of claim 24, wherein said step (a6) comprises the steps of:

(a6i) making a first reading of a fall rate of water within said hollow tube;

(a6ii) making a second reading of a fall rate of water within said hollow tube at a predefined duration of time from performing step (a6i);

(a6iii) making subsequent readings of a fall rate of water within said hollow tube at the predefined duration of time;

(a6iv) determining whether two consecutive readings of a fall rate are substantially equal; and (a6v) if said two consecutive readings of a fall rate are substantially equal in step (a6iv), setting said stable reading fall rate as said two consecutive readings of a fall rate.

* * * * *